(12) United States Patent
Vullings et al.

(10) Patent No.: US 8,332,021 B2
(45) Date of Patent: Dec. 11, 2012

(54) FETAL MONITORING

(75) Inventors: Rik Vullings, Venray (NL); Christiaan Peters, Den Bosch (NL); Swan Gie Oei, Veldhoven (NL); Petrus Wijn, Eindhoven (NL)

(73) Assignees: Stichting Voor de Technische Wetenschappen, Utrecht (NL); Technische Universiteit Eindhoven, Eindhoven (NL)

( * ) Notice: Subject to any disclaimer, the term of this patent is extended or adjusted under 35 U.S.C. 154(b) by 247 days.

(21) Appl. No.: 12/690,377

(22) Filed: Jan. 20, 2010

(65) Prior Publication Data
US 2010/0185108 A1 Jul. 22, 2010

Related U.S. Application Data

(63) Continuation of application No. PCT/EP2008/059468, filed on Jul. 18, 2008.

(30) Foreign Application Priority Data

Jul. 20, 2007 (EP) .................................. 07112841

(51) Int. Cl.
*A61B 5/0444* (2006.01)
(52) U.S. Cl. ...................................................... 600/511
(58) Field of Classification Search .................. 600/511, 600/508–509
See application file for complete search history.

(56) References Cited

U.S. PATENT DOCUMENTS
2005/0267376 A1 12/2005 Marossero et al.

FOREIGN PATENT DOCUMENTS
WO   WO 00/54650       9/2000
WO   WO 2005039410 A1 * 5/2005

OTHER PUBLICATIONS

International Search Report for PCT/EP2008/059468, mailed Dec. 4, 2008.
Written Opinion of the International Searching Authority for PCT/EP2008/059468, mailed Dec. 4, 2008.
Sameni, R. et al., "Multichannel ECG and Noise Modeling: Application to Maternal and Fetal ECG Signals", EURASIP Journal on Advances in Signal Processing, vol. 2007, No. 1, (Jan. 2007), pp. 1-14.
Saadane, I.: "Detection of the abdominal fetal electrocardiogram", [Online], (Dec. 2005), Sections III., 3.1.1.-3.1.3; 3.2-3.3; 4.1 and 4.4.

(Continued)

*Primary Examiner* — Carl H Layno
*Assistant Examiner* — Jessica Sarcione
(74) *Attorney, Agent, or Firm* — Nixon & Vanderhye, PC

(57) ABSTRACT

A system for monitoring a fetus during gestation comprises an input for receiving a plurality of electric signals measured on a surface of a maternal body; and a processor for providing a fetal electrocardiogram based on the received electric signals and based on an orientation of the fetus, wherein the fetal electrocardiogram represents a projection of a fetal cardiac potential vector according to a predetermined projection direction that is fixed with respect to the fetus. The fetal vector electrocardiogram is projected according to the projection direction. An at least partial representation of a fetal vector electrocardiogram is provided in dependence on the plurality of electric signals and indicative of a time path of an electrical field vector generated by a fetal heart of the fetus.

20 Claims, 7 Drawing Sheets

OTHER PUBLICATIONS

Van Oosterom, A. et al., "Lead systems for the abdominal fetal electrocardiogram", Clinical Physics and Physiological Measurement, vol. 10, No. 4B, (Nov. 1, 1989), pp. 21-26.

Ernest Frank, Ph. D., "General Theory of Heart-Vector Projection", Apr. 4, 2007, Downloaded From circes.ahajournals.org at Technical University Eindhoven, Circulation Research, vol. 11, May 1964, pp. 258-270.

Thomas Franciscus Oostendorp, "Modelling the Fetal ECG", Proefschrift, Jul. 20, 1959, Financial Support by Lameris B.V. for Publication of this Thesis, pp. 1-60.

R. Vullings, "The Fetal Electrocardiogram, Determination of the Fetal Heart Rate and Electrocardiogram From Abdominal Recordings", Aug. 2005, Eindhoven University of Technology Faculty of Applied Physics, pp. 1-79.

\* cited by examiner

FETAL MONITORING

This application is a Continuation of International Application No. PCT/EP2008/059468, filed 18 Jul. 2008, which designated the U.S. and claims priority to EP Application No. 07112841.7, filed 20 Jul. 2007, the entire contents of each of which are all hereby incorporated herein by reference.

FIELD OF THE INVENTION

The invention relates to monitoring a fetus during gestation.

BACKGROUND OF THE INVENTION

Generally, during pregnancy, the fetal health condition is monitored by assessing fetal heart rate variability and fetal movements. The degree of fetal heart rate variability provides indirect information on the physiological state of the fetus, e.g. when the fetus is asleep the fetal heart rate variability is expected to be smaller than when the fetus is awake and active. The frequency with which transitions between these physiological states occur is used by physicians to monitor the development of the fetus with progressing pregnancy. As stated, the fetal heart rate variability is an indirect parameter to assess the physiological state of the fetus. Another parameter from which the state can be determined is the degree of fetal movement. However, occurrence of fetal movement can only be established through subjective assessment of the mother or by ultrasonic echo recordings.

During pregnancy, Doppler ultrasound is the most widely used method to monitor the fetal heart rate. However, due to the small size of the fetal heart and vascular system the resolution of the Doppler ultrasound signal is small. Moreover, the ultrasound probe requires frequent repositioning as a result of movement by either the mother or fetus. Another disadvantage of this method is that, when it is combined with ultrasonic fetal movement monitoring, two ultrasound probes are required. Not only is this more demanding for physicians, but also do both these probes feed energy to the fetal body, which potentially affects fetal health.

In "Limitations of autocorrelation in fetal heart rate monitoring" by Fukushima, T. et al., in Am. J. Obstet. Gynecol. 1985; 153:685-692, a fetal heart rate monitor is described that produces a fetal heart rate. Also, autocorrelated ultrasound fetal heart rate records are compared to simultaneously recorded direct scalp fetal electrocardiogram tracings, and the potential misinterpretation of autocorrelated fetal heart rate data is discussed.

SUMMARY OF THE INVENTION

It is an object of the invention to provide an improved system for monitoring a fetus during gestation. In a first aspect of the invention a system is presented that comprises an input for receiving a plurality of electric signals measured on a surface of a maternal body; and means for providing a fetal electrocardiogram based on the received electrical signals and based on an orientation of the fetus, wherein the fetal electrocardiogram represents a projection of a fetal cardiac potential vector according to a predetermined projection direction that is fixed with respect to the fetus.

This allows producing electrocardiograms in a consistent manner, because the fetal electrocardiogram corresponds to a projection direction that is fixed with respect to the fetus. In general, the fetus moves, rotates, and generally changes position within the uterus. This influences the electric signals measured on the surface of the maternal body, and also influences any fetal electrocardiogram derived from these signals. By correcting these signals for the orientation of the fetus, a more consistent measurement is realized. Moreover, it allows to obtain a fetal electrocardiogram that corresponds to a measurement with predetermined positioning of electrodes on the surface of the fetus, without actually requiring to apply these electrodes. This is an advantage, because applying electrodes to a fetus during gestation is usually clinically undesirable and often invasive to the mother and/or invasive to the fetus.

A fetal vector electrocardiogram may be extracted from the measured signal in a way known in the art. The orientation of the fetus may be established by analysis of the fetal vector electrocardiogram, which may be reconstructed from the measured signals. This orientation may also be established by performing a pattern matching of the fetal electrocardiograms derived from the electric signals, as known in the art. The projection of the fetal cardiac potential vector may be computed as a projection of the fetal vector electrocardiogram. It may also be computed as a predetermined transformation of the fetal electrocardiograms derived from the electric signals, wherein the transformation depends on the orientation of the fetus. This predetermined transformation may be determined by means of machine learning techniques that are known in the art, such as neural network techniques and simulated annealing.

An embodiment comprises means for providing an at least partial representation of a fetal vector electrocardiogram in dependence on the plurality of electric signals and indicative of a time path of an electrical field vector generated by a fetal heart of the fetus; and wherein the means for providing a fetal electrocardiogram is arranged for projecting the fetal vector electrocardiogram according to the projection direction.

This is a particularly efficient way to obtain the electrocardiogram relating to the projection direction.

In an embodiment, the projection direction corresponds to a measurement with electrodes attached to a scalp of the fetus. This is a commonly used type of measurement for fetuses, and consequently clinicians are relatively experienced in interpreting this type of fetal electrocardiogram. This embodiment allows to obtain scalp ECG in a way that is non-invasive to the mother and non-invasive to the fetus.

In an embodiment, the projection direction corresponds to at least one direction associated with the Van Einthoven triangle: Lead I, Lead II, Lead III, aVR, aVL, or aVF. This is a commonly used measurement for humans, and consequently clinicians are relatively experienced in interpreting this type of electrocardiogram. It allows for a convenient way to determine the fetal heart rate. The signals corresponding to standard leads may be connected to existing medical equipment that expect these signals as their input. This embodiment allows to obtain the standard leads (I, II, III) and augmented leads (aVR, aVL, aVF) in a way that is non-invasive to the mother and non-invasive to the fetus.

An embodiment comprises means for obtaining an at least partial representation of a fetal vector electrocardiogram indicative of a time path of an electrical field vector generated by a fetal heart of the fetus; and means for establishing orientation information relating to the fetus in dependence on a shape of the fetal vector electrocardiogram according to the at least partial representation.

This system provides an alternative way of monitoring a fetus. The system is more reliable, because the outcome does not depend on subjective assessment of the mother and does not depend on the positioning of an ultrasonic probe by a physician such as a gynecologist or radiologist. The fetal vector electrocardiogram has a three-dimensional shape, and this shape has a more or less fixed orientation with respect to the fetal heart. Consequently, orientation information relating to the fetus can be extracted from the fetal vector electrocardiogram.

In an embodiment, the orientation information is indicative of an orientation of the fetus, in particular the fetal thorax. This is useful diagnostic information.

In an embodiment, the means for establishing orientation information comprises means for comparing the fetal vector electrocardiogram with a reference vector electrocardiogram to establish an orientation of the fetal vector electrocardiogram with respect to the reference vector electrocardiogram. The reference vector electrocardiogram for example represents an average shape of fetal vector electrocardiograms found in a predetermined population of fetuses. Alternatively, the reference vector electrocardiogram represents an earlier measured fetal vector electrocardiogram of the same subject. The comparison may be performed for example using data fitting techniques (leas mean squares optimization), using one or more angles of rotation as data fitting parameters. Comparing of the fetal vector electrocardiogram provides useful information of the orientation of the fetal heart, which is closely related to the orientation of the fetal thorax and the orientation of the fetus.

In an embodiment, the reference vector electrocardiogram is associated with a predetermined orientation, and the means for establishing orientation information comprises means for establishing an orientation of the fetus with respect to the predetermined orientation. By doing this, the orientation of the fetus is found.

In an embodiment, the orientation information is indicative of a motion of the fetus. Motion, in particular rotational motion, or translational motion, can be detected without knowledge of the actual instantaneous orientation at any moment. This allows the system to establish the rotational motion even when the fetal vector electrocardiogram does not contain sufficient information to establish the actual orientation of the fetus. Rotational motion is a useful quantity in relation to fetal monitoring.

In an embodiment, the means for establishing orientation information comprises means for comparing first fetal vector electrocardiogram data obtained during a first time interval with second fetal vector electrocardiogram data obtained during a second time interval to establish the motion of the fetus. This is an effective way of determining the orientation of the fetus. The comparison may be performed for example using data fitting techniques (least mean squares optimization), using one or more angles of rotation as data fitting parameters.

In an embodiment, the orientation information is indicative of an orientation of the fetal heart.

In an embodiment, at least part of the orientation information is relative to an orientation of a maternal body bearing the fetus. This may be automatically the case since the electrodes with which the measurements were acquired, are usually affixed to the maternal body surface.

An embodiment comprises means for transforming electrocardiography data into a projected fetal electrocardiogram according to a predetermined projection direction that is fixed with respect to the orientation of the fetus as indicated by the orientation information.

In an embodiment, the means for obtaining the fetal vector electrocardiogram comprises a plurality of electrodes arranged for being positioned close to a surface of a maternal body bearing the fetus. This allows for a convenient, noninvasive way of acquiring the fetal vector electrocardiogram. Usually the electrodes are positioned on or fixed to the maternal body surface.

In an embodiment, at least one of the electrodes comprises a capacitive electrode. A capacitive electrode is particularly convenient to use. However, any other type of electrode may also be used.

In an embodiment, the means for obtaining the fetal vector electrocardiogram comprises signal processing means for transforming signals from a plurality of electrodes that are arranged for being positioned close to a surface of a maternal body bearing the fetus into the fetal vector electrocardiogram. This is an efficient way of obtaining the fetal vector electrocardiogram.

In an embodiment, the signal processing means comprises a means for removing a maternal electrocardiography signal from at least one of the signals obtained from the plurality of electrocardiography electrodes. This improves the signal to noise ratio of the fetal electrocardiography signal.

In an embodiment, the orientation information is indicative of an orientation of a heart of the fetus, and further comprising a medical imaging apparatus for establishing an orientation of a body of the fetus; and means for establishing an orientation of the heart of the fetus relative to the body of the fetus using a difference between the orientation of the body of the fetus established using the medical imaging device and the orientation of the heart of the fetus established using the vector electrocardiogram.

This helps to determine whether the heart has a, for example, abnormal orientation.

An embodiment comprises at least one of:

a display for showing the established information;

a recorder for storing the established information; or an output for transmitting the established information to another device.

This allows for display, storage, or further processing of the results.

An embodiment comprises a cardiac monitoring device comprising one of the systems set forth.

An embodiment comprises a method of monitoring a fetus during gestation, the method comprising obtaining an at least partial representation of a fetal vector electrocardiogram indicative of a time path of an electrical field vector generated by a fetal heart of the fetus; and establishing orientation information relating to the fetus in dependence on a shape of the fetal vector electrocardiogram according to the at least partial representation.

An embodiment comprises a computer program product comprising machine executable instructions for causing a processor to perform the method set forth.

BRIEF DESCRIPTION OF THE DRAWINGS

These and other aspects of the invention will be further elucidated and described with reference to the drawing, in which.

DETAILED DESCRIPTION OF EMBODIMENTS

Figure 1:
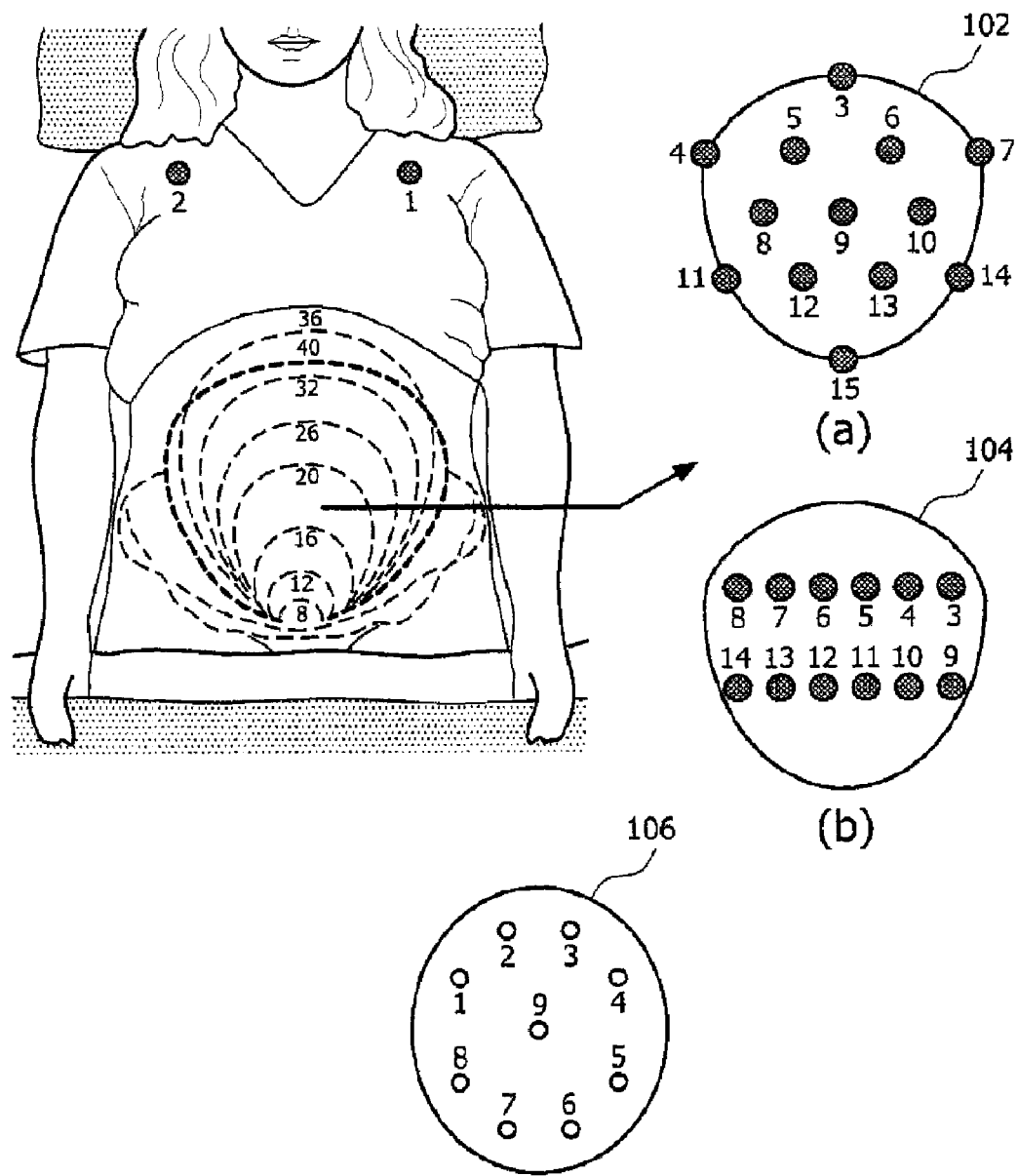
FIG. 1 illustrates electrode configurations.

A major problem in modern obstetrics with respect to fetal monitoring is the limited possibilities to extract information from the fetus to assess its condition. The fetal heart rate is one of very few useful fetal signals that can be measured non-invasively and in many cases in clinical practice the only source of information available.

The fetal heart rate can be determined in several ways, based on two different physical principles. Electrical activity of the fetal heart can be determined by positioning electrodes either directly on the fetus or by positioning electrodes on the maternal abdomen. Positioning the electrodes directly on the fetus is an invasive technique and can only be performed when the fetal membranes have ruptured. Positioning the electrodes on the maternal abdomen is preferable since it is a non-invasive technique, which therefore can be applied in all stages of pregnancy. For example, in "Fetal Electrocardiogram Extraction by Blind Source Subspace Separation" by Lieven De Lathauwer et al., in: IEEE Transactions on Biomedical Engineering, Vol. 47, No. 5, May 2000, the technique of independent component analysis, also known as blind source separation, is proposed as a tool for the extraction of the antepartum fetal electrocardiogram from multi-lead cutaneous potential recordings.

A second physical principle from which the fetal heart rate can be determined is used in Doppler ultrasound measurements. Ultrasonic waves experience a shift in frequency when they reflect and scatter at a moving interface. The magnitude and direction of this shift contains information about the motion of that interface. This effect is known as the Doppler principle. Since the fetal heart moves during contraction, Doppler ultrasound can be used as a non-invasive technique to determine the fetal heart rate. The use of Doppler ultrasound is therefore incorporated in the most widely used device to monitor the fetal heart rate non-invasively, the fetal cardiotocograph monitor.

Next to fetal heart rates, this cardiotocograph (CTG) also monitors uterine activity. As uterine contractions can impose stress on the fetus, the relationship between uterine activity and fetal heart rates can provide information on the fetal condition. This relationship has therefore been investigated extensively through the years. Many guidelines and scoring systems have been proposed for the interpretation of CTG recordings and several of these guidelines are used in clinical practice. However, the information provided by the CTG has turned out to be only sufficient when the condition of the fetus is clearly good or clearly bad. Very often, it is not possible to draw conclusions from CTG recordings and additional tests, such as microblood examination, are required to evaluate the condition of the fetus. Besides the lack of information for accurately evaluating the fetal condition, the use of the CTG is also associated with the drawback that, since it is based on ultrasound, the CTG is very sensitive to motion and noise.

From this it is clear that any additional source of information from which the fetal condition can be assessed or any reliable and accurate alternative to determine the fetal heart rate would be highly appreciated.

The fetal ECG complexes are calculated by subtracting the maternal ECG, detecting the fetal R-peaks and increasing the SNR of the resultant signals by averaging and filtering. Averaging is performed by aligning ten successive fetal ECG complexes by their R-peaks and calculating the average complex, excluding complexes that have a relatively small correlation with the other complexes. To further increase the SNR of the resultant fetal ECG complexes an adaptive filter, working with a moving window, is applied. To evaluate the condition of the fetus, physicians have to interpret ECG leads that are commonly determined for humans. For this reason, the measured ECG complexes have to be transformed to these commonly determined ECG leads. This transformation is performed by reconstructing the fetal vectorcardiogram (VCG) from the recorded ECG leads and by calculating the standard and extremity ECG leads from this VCG.

Maternal uterine activity is calculated by two different methods, based on two different phenomena. First the uterine activity is calculated from the electromyogram (EMG) signals originating from the uterus. Furthermore, uterine activity can be calculated from motion artifacts, caused by deformations of the abdominal surface. Uterine activity is calculated from motion artifacts by applying a high-pass filter on the data signals and summing the activities in all signals. The uterine EMG signal is obtained by applying FastICA, an algorithm based on independent component analysis, on the recorded data and uterine activity is determined from this EMG signal by calculating the contributions of the EMG signal to the recorded signals in the spectral band between 0.6 Hz and 3 Hz.

The fetal heart rates calculated from the abdominal recordings are compared to the heart rates calculated from a simultaneously measured direct fetal ECG, obtained by using a scalp electrode. The correlation coefficient between the abdominally determined heart rates and the directly measured heart rate is 0.998 and the mean value of the differences between them is 0.0±0.7 BPM. Furthermore, the algorithm is capable of calculating 90 percent of the fetal heart rates from all performed measurements, except for gestational ages between 28 and 32 weeks. For these ages the fetus is electrically shielded from its environment by the vernix caseosa, a waxy substance coating the skin of the fetus. As a result of this shielding less than 60 percent of the fetal heart rates can be determined.

The fetal ECG complexes calculated from the fetal VCG show similar waveforms as for the same leads recorded on a healthy human being outside the uterus. Furthermore, the mean P-R/R-R interval length ratio from the abdominally determined fetal ECG complexes agree well with the mean P-R/R-R interval length ratio calculated from the directly measured fetal ECG; the mean value of the differences between instantaneous values is −0.01±0.01. As a result of noise, the agreement between instantaneous values is worse; the correlation coefficient is 0.583. The mean QRS-interval length calculated from the abdominal recordings also agrees well with the mean QRS-interval length determined from the directly measured ECG; the mean value of the differences between instantaneous values is −0.001±0.002 s.

Uterine activity determined from both motion artifacts and uterine EMG signals is consistent with an intra-uterine pressure measurement conducted simultaneously with the abdominal recordings, i.e. bursts in uterine activity calculated from both methods coincide with bursts in the intra-uterine pressure. Difference between both methods is that for the uterine activity calculated from the uterine EMG the SNR is relatively high, but the amplitude of a particular burst with respect to other bursts cannot be determined. In contrast, the uterine activity calculated from abdominal deformations has a relatively low SNR but the amplitude of a particular burst with respect to other bursts can be determined.

The following abbreviations are used throughout this text.
aVF Augmented Voltage lead Foot;
aVL Augmented Voltage lead Left; and
aVR Augmented Voltage lead Right.

At a certain distance the heart can be modeled by a time-dependent dipole with variable amplitude and orientation. At this distance, the ECG can be seen as the projection of the electrical field generated by this dipole on the measurement vector.

The fetal protection mechanism against oxygen deficiency consists of several reactions that enable the fetus to maintain sufficient oxygen supply to central organs, such as the fetal heart and brain. A first reaction to oxygen deficiency is a reduction of fetal activity, i.e. the reduction of fetal movement and fetal respiration. As the lack of oxygen continues, the fetus reacts by redistributing the blood circulation to central organs at the expense of the oxygen supply to peripheral organs. Furthermore, activity of the autonomic nervous system is increased, stimulating anaerobe metabolism in the peripheral organs. When the fetal protection is fully intact, the fetus reacts optimally to hypoxemia (a decrease of the arterial blood oxygen level) and acute hypoxia during labor, minimizing the risk of damage. When fetal protection is missing, minimal reaction to hypoxia is observed since most of the defensive mechanisms have been used already or did not have had the opportunity to develop. In this case the risk of damage as a result of asphyxia (global oxygen deficiency including the central organs) is significant and several non-characteristic signs of fetal distress can be expected.

Consequently, fetal monitoring during labor has become very important and has enabled physicians to take action when fetal protection is activated but when an increased risk of long-term consequences exists.

The fetal heart rate can be determined in several ways, based on two different physical principles. Electrical activity of the fetal heart can be determined by positioning electrodes either directly on the fetus or by positioning electrodes on the maternal abdomen. Positioning the electrodes directly on the fetus is an invasive technique and can only be performed when the fetal membranes have ruptured. Positioning the electrodes on the maternal abdomen is preferable since it is a non-invasive technique, which therefore can be applied in all stages of pregnancy. However, due to the low signal-to-noise ratio, determination of the fetal heart rate from abdominal recordings with existing techniques is inaccurate and not reliable.

Next to fetal heart rates, the cardiotocograph (CTG) monitors uterine activity. As uterine contractions can impose stress on the fetus, the relationship between uterine activity and fetal heart rates can provide information on the fetal condition. This relationship has therefore been investigated extensively through the years. Many guidelines and scoring systems have been proposed for the interpretation of CTG recordings and several of these guidelines are used in clinical practice. However, the information provided by the CTG has turned out to be only sufficient when the condition of the fetus is clearly good or clearly bad. Very often, it is not possible to draw conclusions from CTG recordings and additional tests, such as microblood examination, are required to evaluate the condition of the fetus. Besides the lack of information for accurately evaluating the fetal condition, the use of the CTG is also associated with the drawback that, since it is based on ultrasound, the CTG is very sensitive to motion and noise.

The information, obtained by using electrodes on the maternal abdomen, is superior to Doppler ultrasound recordings in several aspects. Not only are the abdominal recordings more reliable in the sense that they are much less sensitive to motion, but as a result the obtained fetal heart rate signal is almost a continuous signal without blank periods requiring interpolation, as is often the case with ultrasound recordings. Spectral analysis, performed on abdominal recordings, is therefore more accurate. Finally, the abdominal recordings provide additional information with respect to ultrasound recordings by means of the fetal ECG. Besides the more reliable and additional information, electrical recordings on the maternal abdomen have one more advantage over ultrasound recordings: electrical recordings do not feed energy to the fetal and maternal body.

Measurements are preferably performed using several Ag/AgCl electrodes positioned on the shoulders and abdomen of the mother. However, any kind of electrodes may be used, including non-contact electrodes such as capacitive electrodes. Three different electrode configurations 102, 104, and 106 are shown in FIG. 1 as examples. Configurations 102 and 104 use two electrodes 1 and 2 on the shoulders and the remaining electrodes on the abdomen as indicated. Since the amplitude of the fetal signal is not equal across the maternal abdomen, configuration 104 has two transversal lines of six electrodes each on the abdomen, to ensure having at least one electrode in the vicinity of an optimal measuring position. This allows to obtain the fetal electrocardiogram (ECG) and fetal heart rate from the abdominal recordings. In configuration 102 electrodes are positioned on the abdomen in such a way as to cover as much uterine surface area as possible. This way, it is possible to analyze which positions provide the highest fetal ECG amplitude. It is advantageous to reduce the number of electrodes because of efficiency, patient comfort, cost, and processing power needed to perform signal processing. To this end, configuration 106 shows nine electrode positions covering the maternal abdomen. In configuration 106, electrode 9 is a grounding electrode used in conjunction with the other electrodes 1-8, and an additional grounding electrode is used (not shown). In configuration 106, electrodes on the shoulders of the mother are not used.

Fetal electrophysiological signals are calculated from abdominal recordings according to an algorithm that operates in two steps. First step is the subtraction of the maternal electrocardiogram (ECG), filtering of the 50 Hz power line interference and elimination of the baseline drift. The second step consists of the detection of fetal R-peaks. Measurements are performed using twelve electrodes positioned on the maternal abdomen. In general any number of electrodes may be used that allows to obtain spatial information such as orientation information, for example configuration 106 may be used. One reason for using a plurality of electrodes is that the signal-to-noise ratio of particular electrodes is high with respect to the other electrodes, depending on the position of the fetal heart. However, due to relatively large computation times, it is desirable to reduce the number of signals processed by the algorithm.

In order to achieve this, at first the algorithm performs a so-called initialization in which the signals containing the largest fetal component are determined. The data obtained from the abdominal recordings are a mixture of electrophysiological signals and noisy interferences. One of the main noisy components is the 50 Hz powerline signal, which is cancelled out by the application of a fourth order Butterworth bandstop filter, filtering between frequencies of 48 Hz and 52 Hz. Since the signals of interest are in the range between 2 Hz and 80 Hz, harmonics of the powerline signal are cancelled out using a fourth order Butterworth low-pass filter with cut-off frequency of 90 Hz. The baseline wander of the signals is cancelled out by the application of a fourth order Butterworth high-pass filter with cut-off frequency of 1.5 Hz. All filters are applied in both forward and backward directions to compensate for phase shifts. Alternatively FIR filters may be used, for example 1000 tap linear phase FIR filters.

After filtering the data, the next step is the removal of the maternal ECG. The amplitude and morphology of the fetal ECG depend on the position of the electrode with respect to the position of the fetal heart. Therefore, the fetal ECG is not detected with equal amplitudes by all electrodes. In order to determine which electrodes detect the largest fetal signal, the location of the fetal R-peaks has to be known. The processed data from the electrodes are combined and linearly transformed into independent components, for example by using the FastICA algorithm. The FastICA algorithm is a known blind source separation technique based on the principle of Independent Component Analysis (ICA). Since the fetal ECG is uncorrelated and statistically independent of the maternal ECG and other noisy interferences, one of the independent components, as determined by FastICA, represents the fetal ECG signal.

A preferred way to determine the heart rate from an ECG signal is by measuring the time between the start of the depolarization at the SA-node of two successive heartbeats. In a standard ECG, this is expressed by the start of the P-wave. Due to noise in fetal ECG signals, it is not always possible to detect the start of this wave accurately. For this reason, the time between two successive R-peaks is used to determine the instantaneous heart rate. The use of the R-wave simplifies the determination of the heart rate but, due to variations in P-R interval length, additional jitter may occur.

The algorithm, suitable for online monitoring of the fetal heart rate, processes the data collected by the four electrodes with the largest fetal component in the signal. However, any desired number of electrodes may be used instead of four. First step of the algorithm is the subtraction of the maternal ECG using segmentational adaptive averaging. The signals obtained after subtraction are averaged, regarding the SNR and polarity of the fetal ECG in the signal:

$$\overline{fecg(n)} = \frac{\sum_{i=1}^{4} pol_i \cdot SNR_i \cdot fecg_i(n)}{\sum_{i=1}^{4} SNR_i},$$

wherein $fecg_i(n)$ is the fetal ECG as determined by subtraction of the maternal ECG, $pol_i$ is the polarity of the fetal R-peaks and is equal to $\pm 1$. $SNR_i$ is the signal-to-noise ratio of the fetal ECG. $\overline{fecg(n)}$ is the average of the fetal ECG.

Under some circumstances, the estimated maternal ECG complex can incorporate part of the fetal ECG complex. These situations occur when the amplitudes of the peaks in the maternal ECG are affected by the fetal ECG. In these situations subtraction of the estimated maternal ECG results in the partial or complete subtraction of the fetal ECG. To guarantee a sufficient signal-to-noise ratio for all peaks in the averaged fetal ECG, the maternal ECG is estimated again using for example linear prediction. In this step the ECG complex is averaged as a whole. For this reason, the fetal ECG complex does not affect the maternal ECG estimate. The fetal R-peaks are detected using a peak detection algorithm. The instantaneous fetal heart rate is calculated from the time between two successive R-peaks.

For example, N=20 preceding ECG complexes are used to estimate the morphology of a particular complex. These preceding complexes are stored in a small database containing 20 complexes for each of the four signals used by the online monitoring algorithm. In order to deal with significant changes in the morphology of the measured maternal ECG complex over time, the database is updated continuously replacing the oldest complex with the newest one. Any suitable value of N may be used instead of 20.

In some situations the order of magnitude of the averaged fetal R-peak amplitudes is about the same as the order of magnitude of the noise. In these situations, it is possible that noise is detected as fetal R-peak. To reduce this possibility, the detected peak locations are verified by checking whether the interval between two successive peaks is within a certain deviation, i.e. 20 percent, from the mean interval length. To guarantee a reliable mean interval length, a sufficiently large number of fetal R-peaks have to be present in the processed data set.

The fetal ECG complex is determined from the signals resulting from the subtraction of the maternal ECG complex, and defined analogously to the definition of the maternal ECG complex. That is, after the abdominal recordings have been filtered to remove the powerline interference and baseline drift and after the maternal ECG has been subtracted, the fetal R-peaks are detected and each fetal ECG complex is defined as the interval between two successive triggers. These triggers are defined as the point in time 0.40T, with T the mean R-R interval length, before a fetal R-peak. Due to the relatively low signal-to-noise ratio of the fetal ECG, it may not be possible to extract particular features, such as intervals lengths, from the complex. Improvement of the SNR is obtained in a few post processing steps.

First, the individual fetal ECG signals are subtracted from each other to obtain specific ECG leads. Next, for a specific lead, each normalized ECG complex is cross-correlated with N−1 preceding complexes. N is herein, for example, set equal to N=10. Since the maximal amplitude of the correlation supplies information about the similarity of the complexes, averaging the complexes while excluding complexes with a relatively low correlation, results in a higher SNR. The final step in improving the SNR of the fetal ECG complex is the application of an adaptive filter.

Peak detection of ECG signals may be performed in a way known in the art.

A central problem in signal processing is finding a suitable representation of the data, by means of a linear transformation. A particular method of finding the linear transformation is called independent component analysis (ICA). As the name implies, the basic goal of ICA is to determine a transformation in which the components are statistically as independent from each other as possible. ICA can be applied, for instance, for blind source separation. Usually, electrophysiological and noisy signals are statistically independent from each other and thus these signals can be recovered from linear mixtures by finding a transformation in which the transformed signals are as independent as possible. ICA is a method that is known in the art. The FastICA algorithm has been developed for performing the computations needed for ICA. FastICA is described in "Fast and robust fixed-point algorithms for independent component analysis" by A. Hyvärinen, IEEE Trans. on Neural Networks 10(3):626-634, 1999, hereinafter referred to as "Hyvärinen 1999".

In some cases, the original recordings have fetal ECG complexes with the same order of magnitude as the background noise. Consequently, the retrieved fetal ECG is affected by a low signal-to-noise ratio (SNR). These ECG complexes can be enhanced by using a smoothing procedure based on a filter working with a moving window.

The determination of the maternal heart rate is similar to determination of the fetal heart rate.

The recorded ECG leads are difficult to interpret clinically since these leads are not the standard leads that are usually recorded from a patient. For interpreting the fetal ECG complex and obtaining additional information on the condition of the fetus, the ECG is preferably presented in a similar format as common for ECG signals of patients outside the uterus. Examples of these usual ECG leads are the standard leads (I, II and III) in the Einthoven triangle and the extremity leads (aVR, aVL and aVF), all shown in FIG. 2B. The arrows in FIG. 2A illustrate projections corresponding to the standard leads I, II, and III.

The ECG complex is composed of electrical potentials that are generated by the heart and recorded at the skin surface. As differences between electrical potentials of several areas of the heart can be represented by an electrical field vector, the ECG can be described as the projection of this so-called cardiac vector on a particular lead. FIG. 2 shows, the projection 202 of the course of the cardiac vector, known as the vectorcardiogram (VCG), on the plane of measurement and the projection 104 of an instantaneous vector that is part of the VCG 202. A particular lead of the ECG is defined as the length of the projection of the cardiac vector 204 on this lead. This is illustrated in FIG. 2 for standard leads I, II and III.

Figure 2A:
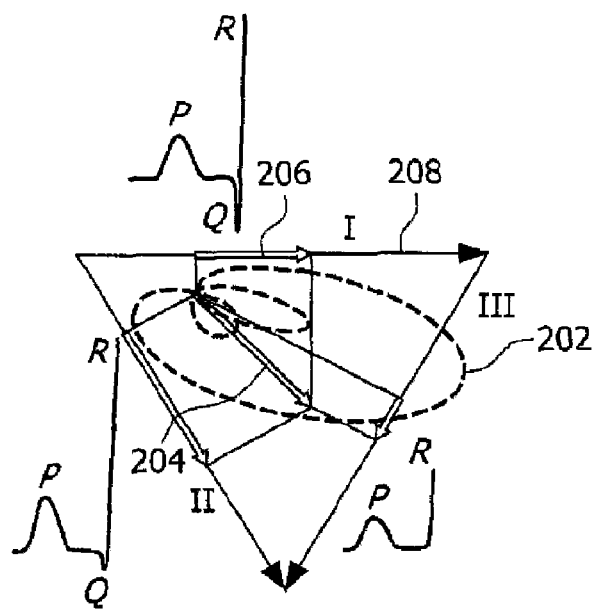
FIG. 2A illustrates a vector electrocardiogram and standard projections.
Figure 2B:
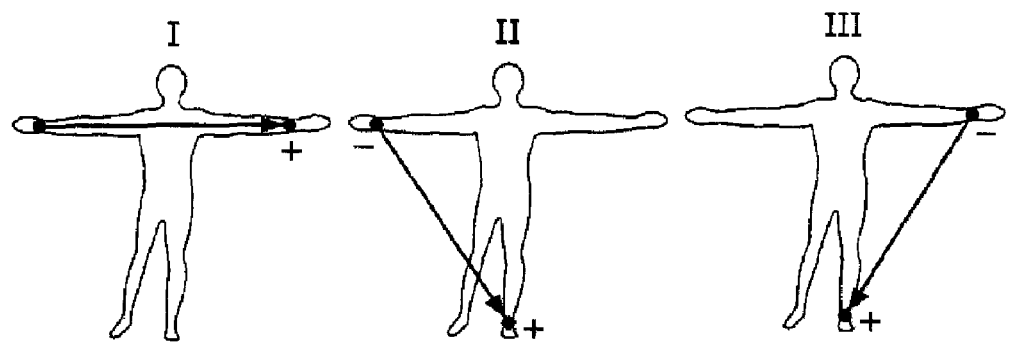
FIG. 2B illustrates standard projections including augmented projections.
Figure 2B:
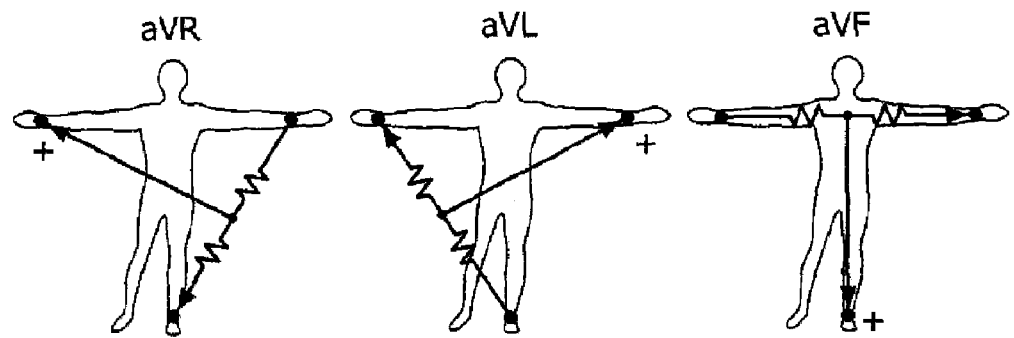

FIGS. 2A and 2B illustrate the Einthoven leads I, II and III and the extremity leads aVR, aVL and aVF. Einthoven assumed the human body to constitute an equilateral triangle with the heart in the center of this triangle. ECG leads are obtained by the projection of the cardiac vector 104 on these leads (e.g. the projection 206 on arrow 208). At 202, the course of the cardiac vector, known as the vectorcardiogram, is projected on a two-dimensional plane.

As the orientation of the fetus in the uterus is generally unknown, it is not easy to position the electrodes in such way that the standard and extremity leads of the fetal ECG can be obtained directly. However, by reconstructing the VCG from the leads that are obtained by the electrode configurations of FIG. 1, it is possible to derive the standard and extremity leads.

Figure 3:
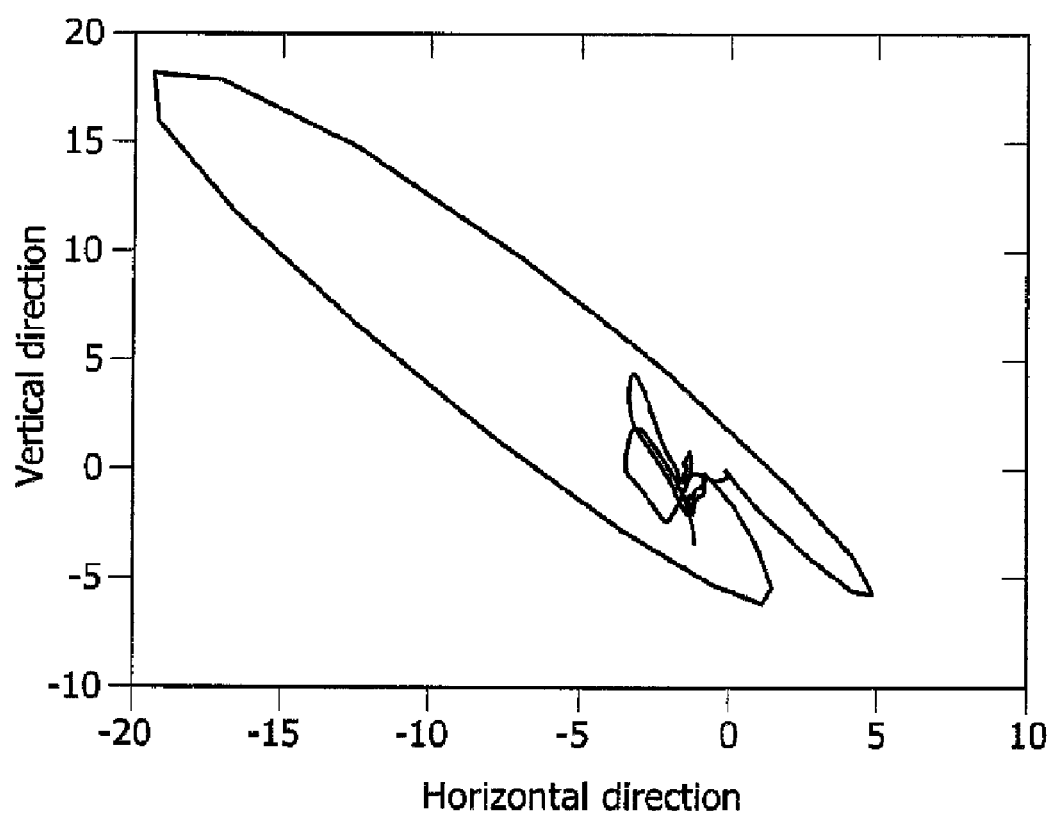
FIG. 3 illustrates a fetal vector electrocardiogram.

FIG. 3 shows a fetal vectorcardiogram resulting from linearly combining the lead vectors of the electrode configuration 104 (after several processing steps to remove the maternal ECG and to improve the signal-to-noise ratio). This vectorcardiogram is the two-dimensional projection on the plane of measurement of the actual course of the cardiac vector. The horizontal direction on the x-axis represents the direction from right to left on the abdomen and the vertical direction on the y-axis represents the direction from feet to head.

Reconstructing the cardiac vector is performed by linearly combining the projections of the cardiac vector on the recorded leads. For each point in time all the lead vectors are multiplied by the amplitude in the corresponding ECG complex and summed to obtain the resultant vector. This resultant vector however has to be normalized for the used lead vectors. The course of the normalized resultant vector, the VCG, is shown in FIG. 3. FIG. 3 does not show the complete cardiac vector but rather the projection of this vector on a plane, in this case the plane of measurement. In spite of the use of averaging and filtering to enhance the SNR of the fetal ECG complex, the VCG may still be significantly affected by noise, in particular for low amplitude intervals in the ECG complex such as the P-Q interval and the S-T interval. To enhance the SNR of these intervals and obtain a rather constant SNR over the complete ECG complex, the amplitude of each sample in a low amplitude interval is averaged with the amplitudes of its adjoining samples.

In contrast to the VCG, as shown in FIG. 2, the orientation of the VCG of FIG. 3 is directed upwards. This can be explained by the fact that the fetus is positioned upside down in the uterus. Furthermore it can be seen that the VCG of FIG. 3 is compressed with respect to the VCG of FIG. 2. This is caused by an angle between the actual cardiac vector and the plane of measurement, resulting in a more compressed projection.

Figure 4:
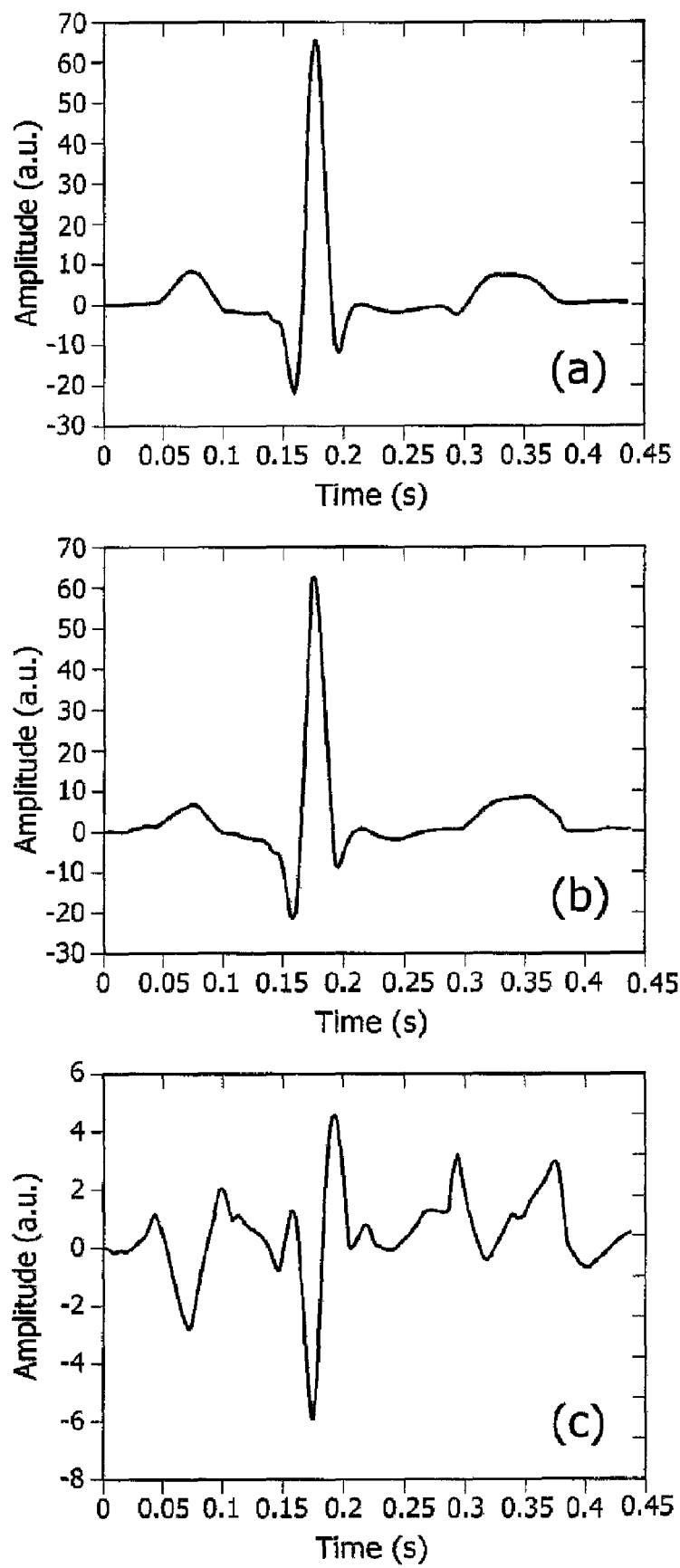
FIG. 4 illustrates standard lead fetal electrocardiograms.
Figure 4:
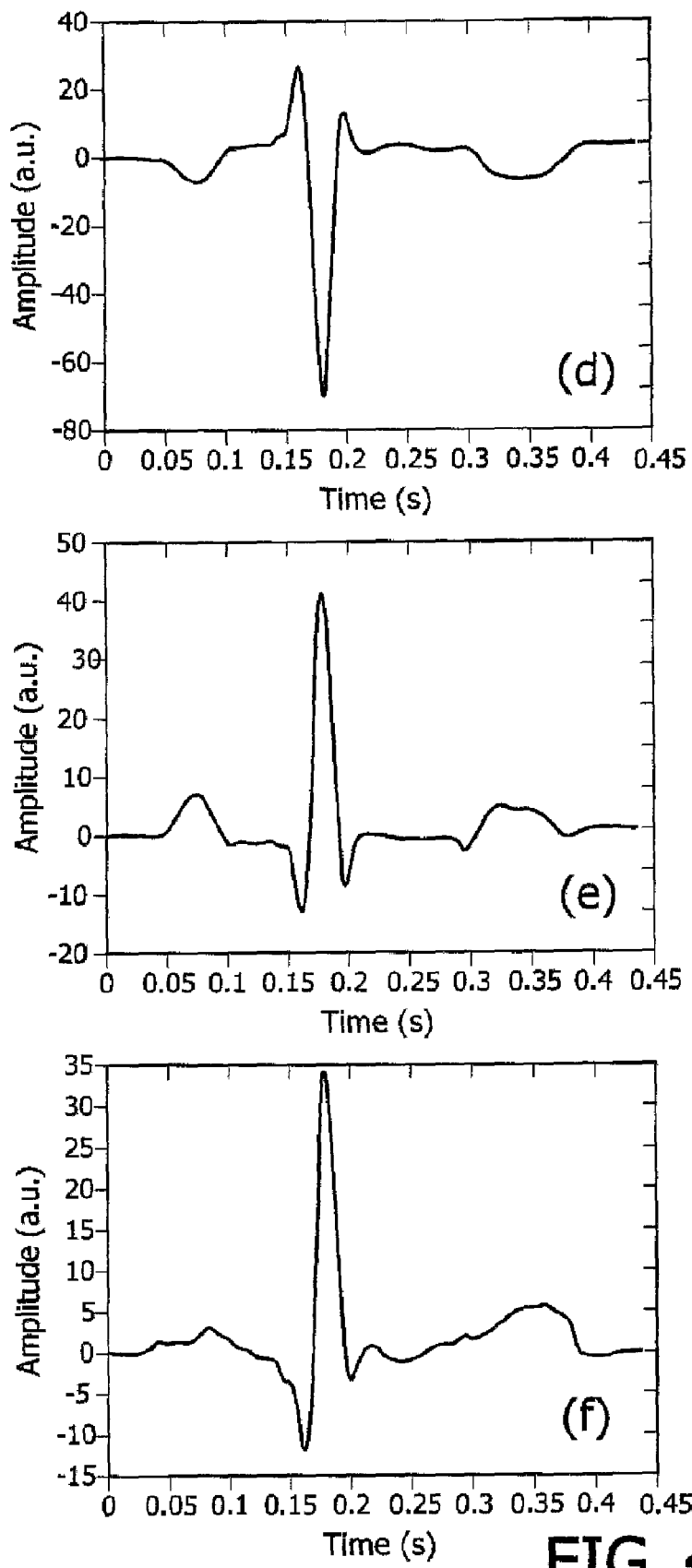

FIG. 4 shows examples of fetal ECG signals determined from the vectorcardiogram of FIG. 3 and corresponding to the standard leads of FIGS. 2A and 2B. FIGS. 4 (a), (b) and (c) show the standard Einthoven leads I, II and III, respectively. FIGS. 4 (d), (e) and (f) show the extremity leads aVR, aVL and aVF, respectively. FIG. 4 shows the standard and extremity leads of the fetal ECG, determined by the projection of the VCG of FIG. 3 on the corresponding lead vectors. In order to obtain the correct projections, the VCG has been rotated around its origin to align with a VCG that is measured outside the uterus. Herein, the origin corresponds to the isoelectrical intervals of the ECG that have zero net potential and therefore a zero cardiac vector.

The vertical scaling of the fetal ECG complexes of FIG. 4 is set to arbitrary units since the measurement and processing do not provide absolute values, but rather provide a normalized signal. Reason for this is that the reconstruction of the VCG does not at present take into account differences in the attenuation of potentials at different recording positions. Because of tissue inhomogeneities and differences in the distance between the fetal heart and the electrode positions, signal attenuation is expected to be different for all electrodes positions. Not considering these differences in attenuation when reconstructing the VCG may cause small errors in the shape of the VCG and the shape of the calculated standard and extremity leads. These errors may be reduced or avoided by taking into account these tissue inhomogeneities and the distance between the fetal heart and the electrode positions. For example, the fetal heart position may be estimated in a first processing step or by means of a medical imaging technique such as ultrasound. The tissue inhomogeneities may be estimated based on a tissue model, which may be refined by using a medical imaging technique such as ultrasound or MRI.

The fetal ECG complexes of FIG. 4 (a,b,d,e,f), corresponding to the standard leads I and II and extremity leads aVR, aVL and aVF, show similar waveforms as when the same leads are recorded on a healthy human being outside the uterus. On the other hand, standard lead III as shown in FIG. 4(c) has opposite polarity for the fetal ECG as for the same lead recorded outside the uterus. This might be caused by inaccurate alignment of the VCG, resulting in a different projection for this lead. This argumentation is validated by the fact that the amplitude of this lead is relatively small, indicating an almost perpendicular projection. Therefore, small deviations in the alignment of the VCG can result in a change in the polarity of the ECG complex.

Reconstruction of the vectorcardiogram also serves for reducing the number of electrodes positioned on the maternal abdomen. As mentioned previously, the bipolar lead providing the maximal deflection of the fetal R-peak can be determined quite easily from the vectorcardiogram. Combining the vectorcardiograms for many patients will therefore probably result in a reduced set of electrode positions, providing fetal ECG signals with a SNR high enough to calculate the fetal heart rate from.

The development of the vernix caseosa at gestational ages of about 28 weeks does not only affect the amplitude of the fetal signal and therefore the determination of the fetal heart rate, but also has significant effect on the calculation of fetal ECG complexes. As gaps in the vernix appear from gestational ages of about 32 weeks, attenuation of the fetal ECG signal is not constant for all electrodes, causing erroneous reconstruction of the vectorcardiogram. The gaps in the vernix are presumably formed around the fetal mouth and umbilicus causing the amplitudes of the leads resembling extremity lead aVF to be high with respect to the amplitudes of other leads. This information can be used to improve the quality of the vectorcardiogram.

The reconstruction of the fetal vectorcardiogram from the abdominal recordings provides a tool to calculate an approximation of the standard ECG leads and the extremity leads as if they were measured on the body of the fetus.

Preferably, differences in attenuation of the fetal ECG signal as a result of different distances between the fetal heart and the electrodes are also considered when determining the fetal vectorcardiogram and/or when deriving orientation information of the fetus. Furthermore, the influence of the vernix caseosa, may result in additional differences in attenuation by electrically shielding some parts of the fetal body. Preferably, this effect is taken into account in the computations. However, this is not required because even without taking into account the different distances and the vernix caseosa, the obtained standard ECG leads and extremity leads may show a good resemblance to the corresponding ECG leads of a healthy human being outside the uterus. This is particularly true for Einthoven leads I and II and the extremity leads aVR, aVL, and aVF.

Next to providing a tool to calculate the standard ECG leads and the extremity leads, the vectorcardiogram serves another purpose. The direction for which the vectorcardiogram has maximum amplitude, and more generally, the overall shape of the vectorcardiogram, is an indication of the direction of the electrical axis of the fetal heart. So for a fetus with a normal electrical axis, the vectorcardiogram provides a tool to determine the orientation of the fetus inside the uterus. Alternatively, if the orientation of the fetus is known, the vectorcardiogram provides a tool to determine the orientation of the heart in the fetus.

For minimizing patient discomfort the number of electrodes positioned on the patient may be reduced. The fetal VCG and the signal-to-noise ratios of the bipolar ECG leads resulting from this VCG can be used to determine which electrode positions provide signals with high enough fetal ECG amplitudes to calculate fetal heart rates, fetal ECG complexes and maternal uterine contractions from. Consequently, evaluating the fetal VCG and corresponding bipolar ECG leads for several measurements can result in a smaller selection of electrode positions providing signals that are good enough to perform the required calculations.

To improve the accuracy of the calculation of the fetal vectorcardiogram from the ECG leads on the abdominal surface, differences in signal attenuation resulting from differences in the distance between electrode positions and the fetal heart may be taken into account. The same holds for the influence of the vernix caseosa. Considering the attenuation of each signal helps to improve the calculation of the vectorcardiogram.

Independent component analysis (ICA) is a statistical signal processing technique for separating a combined set of data into independent components. Assume a set of observations of n random variables $[x_1(t), x_2(t), \ldots, x_n(t)]$, that is generated by a linear instantaneous mixture of m independent components $[s_1(t), s_2(t), \ldots, s_m(t)]$. This can be written as:

$$\begin{pmatrix} x_1(t) \\ x_2(t) \\ K \\ K \\ x_n(t) \end{pmatrix} = A \begin{pmatrix} s_1(t) \\ s_2(t) \\ K \\ K \\ s_m(t) \end{pmatrix},$$

in which $A=[a_1, \ldots, a_m]$ is a constant full-rank [n×m] matrix called the mixing matrix. ICA consists of estimating the matrix A and the sources $s_i(t)$ from the observed) $x_j(t)$. This problem can be solved under the condition that the number of observations n is larger than or equal to the number of independent components m. Typically, ICA methods estimate the unmixing matrix W:

$$\begin{pmatrix} s_1(t) \\ s_2(t) \\ K \\ s_3(t) \end{pmatrix} = W \begin{pmatrix} x_1(t) \\ x_2(t) \\ K \\ K \\ x_n(t) \end{pmatrix},$$

in which $s_i(t)$ be as independent as possible for $i=1, \ldots, m$.

To estimate the independent sources $s_i(t)$ from the linear mixture, ICA uses the principle that statistically independent signal components tend to be characterized by probability distributions that are not Gaussian. In order to solve this problem for fetal ECG signals, the fixed point ICA algorithm FastICA may be used because of its efficiency from the point of view of computational effort. Starting from the definition of a single independent component:

$$s_i(t) = w^T x = \sum_{j=1}^{n} w_j x_j. \tag{Equation 1}$$

FastICA uses the kurtosis of the signals as a measure to determine the Gaussianity of the probability distributions, i.e., the amount to which the probability distributions resemble a Gaussian distribution. This kurtosis is defined for a zero-mean random variable v as $$\mathrm{kurt}(v) = E\{v^4\} - 3(E\{v^2\})^2.$$

Kurtosis is approximately zero for a Gaussian random variable, positive for probability distribution peaked at zero and negative for distribution flatter than Gaussian distributions. This means that kurtosis is suitable to assess the statistical independence of given variables. In order to maximize and/or minimize the kurtosis under the constraint $\|w\|=1$, the natural gradient method can be used. This method has the following learning rule:

$$w(t+1) = w(t) \pm \mu(t)[x(t)(w(t)^T x(t))^3 - 3\|w(t)\|^2 w(t) + f(\|w(t)\|^2) w(t)], \tag{Equation 2}$$

in which x(t) is the sequence of recorded signals, µ(t) is the learning rule and f is a penalty term due to the constraint $\|w\|=1$. Before applying the learning rule, the recorded signals x(t) are preprocessed by means of centering and whitening. Centering is performed by subtracting the mean value to obtain zero-mean signals. Whitening is a linear transformation of the vector x(t) into another vector x*(t), whose components are uncorrelated and have variances equal to unity. The learning rule stops at a fixed point for which $|w^T(t)w(t-1)|$ is sufficiently close to unity. The linear combination $w^T x$ is now one of the required independent components, as stated in equation 1.

The FastICA algorithm is derived from equation 2 and consists of:
1. randomly choosing an initial vector w(0) with unit norm,
2. applying the fixed point iteration rule $w(t)=E\{x(w(t-1)^T x)^3\}-3w(t-1)$ to approximate w(t), with $E\{y\}$ the expected value of y,
3. normalizing w(t) and
4. repeating points 2, and 3. until $|w^T(t) w(t-1)|$ is sufficiently close to unity.

One ICA basis vector is then estimated. Other ICA basis vectors can be estimated by sequentially projecting a new starting basis vector w(0) onto the subspace, orthogonal to the ones covered by the previous vectors.

The reconstruction of the projection of the fetal vectorcardiogram on the maternal abdomen may serve as a method to calculate common recorded ECG leads, which can be clinically interpreted by a physician to obtain information on the condition of the fetus. Since the position and orientation of the fetus inside the uterus are unknown, the electrode positions on the maternal abdomen often constitute uncommon leads, which nevertheless can be used to reconstruct the vectorcardiogram.

The projection of the fetal vectorcardiogram on the plane of measurement (i.e., the surface of the maternal abdomen) may be computed as follows:

$$p_x(t) = \frac{1}{\Delta}\begin{vmatrix} V_1(t) & V_2(t) \\ a_y & b_y \end{vmatrix},$$

and $$p_y(t) = -\frac{1}{\Delta}\begin{vmatrix} V_1(t) & V_2(t) \\ a_x & b_x \end{vmatrix},$$

wherein $$\Delta = \begin{vmatrix} a_x & a_y \\ b_x & b_y \end{vmatrix}.$$

Herein, $V_i(t)$ (for $1=1,2$) is a bipolar fetal ECG signal recorded at electrode i. $(a_x, a_y)$ is a measurement vector for i=1 and $(b_x, b_y)$ is a measurement vector for i=2. $(p_x(t), p_y(t))$ represents the fetal vectorcardiogram in 2D.

Preferably, the vectorcardiogram is computed in 3D rather than the projection on the plane of measurement, because this helps to better estimate the orientation of the vectorcardiogram. The vectorcardiogram can be reconstructed in 3D as follows. As stated previously, the fetal ECG originates from the projection of the three-dimensional fetal VCG on the measurement vector:

$$V_i(t) = \vec{A}_i \cdot \vec{p}(t),$$

with $V_i(t)$ the fECG amplitude at electrode i, $\vec{A}_i$ the measurement vector for electrode i, and) $\vec{p}(t)$ a three-dimensional vector describing the time-path of the electrical field vector generated by the fetal heart: the fVCG. As $\vec{p}(t)$ can be factorized into three components $p_x(t)$, $p_y(t)$, and $p_z(t)$, three independent fECG signals with their corresponding measurement vectors are required to determine) $\vec{p}(t)$:

$$V_1(t) = \vec{A}_1 \cdot \vec{p}(t) = A_{1x} \cdot p_x(t) + A_{1y} \cdot p_y(t) + A_{1z} \cdot p_z(t)$$

$$V_2(t) = \vec{A}_2 \cdot \vec{p}(t) = A_{2x} \cdot p_x(t) + A_{2y} \cdot p_y(t) + A_{2z} \cdot p_z(t)$$

$$V_3(t) = \vec{A}_3 \cdot \vec{p}(t) = A_{3x} \cdot p_x(t) + A_{3y} \cdot p_y(t) + A_{3z} \cdot p_z(t)$$

This linear system can be solved for $p_x(t)$, $p_y(t)$, and $p_z(t)$, resulting in $$p_x(t) = \frac{1}{\Delta}\left[ V_1(t)\begin{vmatrix} A_{2y} & A_{2z} \\ A_{3y} & A_{3z} \end{vmatrix} - V_2(t)\begin{vmatrix} A_{1y} & A_{1z} \\ A_{3y} & A_{3z} \end{vmatrix} + V_3(t)\begin{vmatrix} A_{1y} & A_{1z} \\ A_{3y} & A_{3z} \end{vmatrix} \right]$$

$$p_y(t) = \frac{1}{\Delta}\left[ -V_1(t)\begin{vmatrix} A_{2x} & A_{2z} \\ A_{3x} & A_{3z} \end{vmatrix} + V_2(t)\begin{vmatrix} A_{1x} & A_{1z} \\ A_{3x} & A_{3z} \end{vmatrix} - V_3(t)\begin{vmatrix} A_{1x} & A_{1z} \\ A_{2x} & A_{2z} \end{vmatrix} \right]$$

$$p_z(t) = \frac{1}{\Delta}\left[ V_1(t)\begin{vmatrix} A_{2x} & A_{2y} \\ A_{3x} & A_{3y} \end{vmatrix} - V_2(t)\begin{vmatrix} A_{1x} & A_{1y} \\ A_{3x} & A_{3y} \end{vmatrix} + V_3(t)\begin{vmatrix} A_{1x} & A_{1y} \\ A_{2x} & A_{2y} \end{vmatrix} \right],$$

wherein $$\Delta = A_{1x}\begin{vmatrix} A_{2y} & A_{2z} \\ A_{3y} & A_{3z} \end{vmatrix} - V_{1y}\begin{vmatrix} A_{2x} & A_{2z} \\ A_{3x} & A_{3z} \end{vmatrix} + V_{1z}\begin{vmatrix} A_{2x} & A_{2y} \\ A_{3x} & A_{3y} \end{vmatrix}.$$

The use of more than three bipolar abdominal leads may cause the occurrence of an overdetermined system of equations. Also, inaccuracies may be present due to noise on the fECG complexes. Known methods for solving inverse problems may be used to overcome these inaccuracies.

Figure 5:
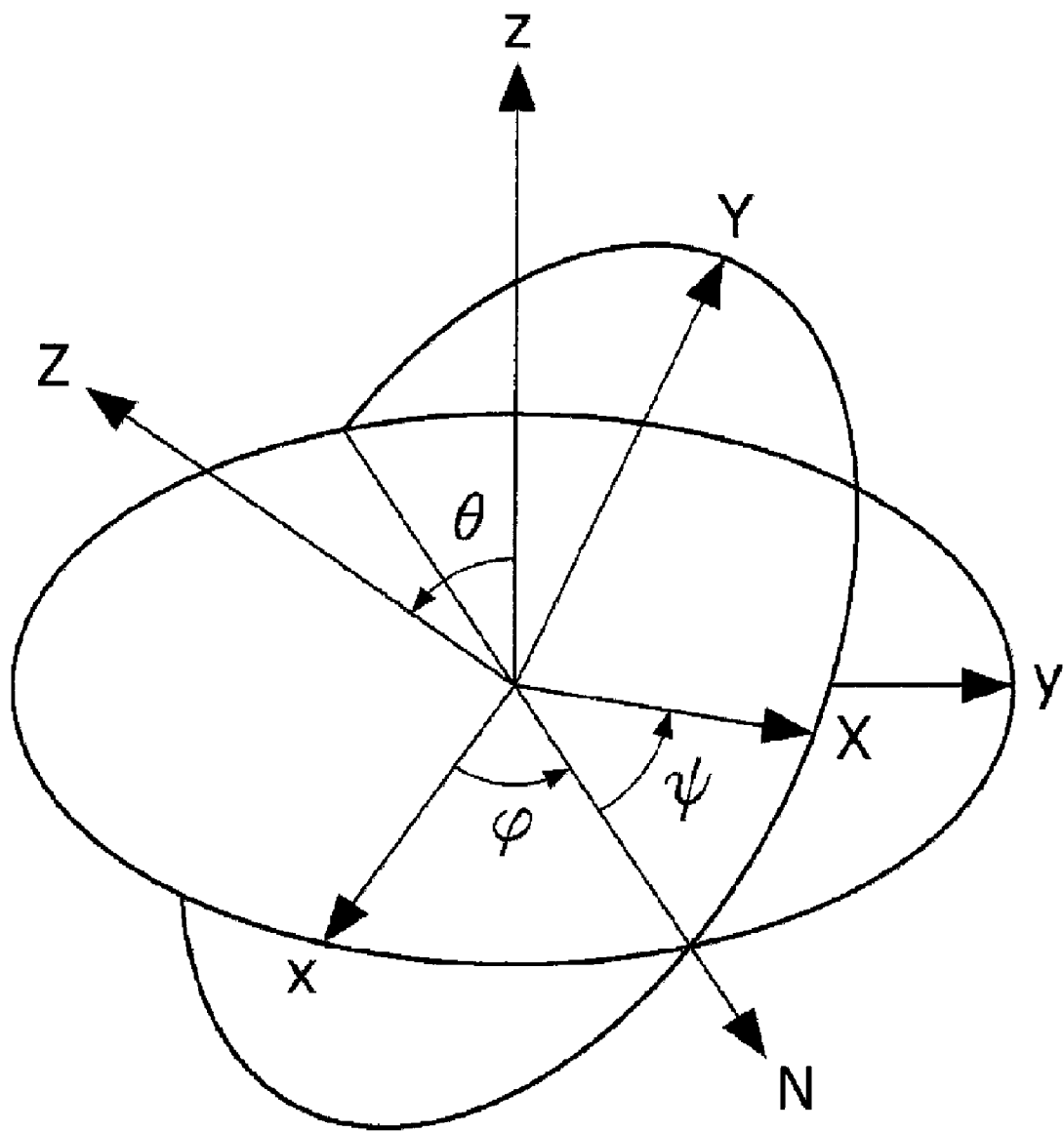
FIG. 5 illustrates three axes of rotation.

FIG. 5 shows a system of axes illustrating a method of fetal movement monitoring through electrophysiological recordings from the maternal abdomen. In an embodiment, the following steps are used to detect fetal movement:
1. Estimation and subsequent subtraction of the maternal ECG. This results in a fetal ECG signal with sufficiently large signal.
2. Calculation of the fetal vectorcardiogram from the combined fetal ECG and spatial electrode information, as described above.
3. Detection of rotation, performed by comparing at least two fetal vectorcardiograms corresponding to different heart beats of the same fetus. The angles of rotation are, for example, determined by trial-and-error. For example, a large number of combinations of the three Euler angles φ, θ, and ψ, indicated in FIG. 5, are tried by rotating one of the two fetal vectorcardiograms according to the Euler angles and comparing the rotated fetal vectorcardiogram with the other one of the two fetal vectorcardiograms. For example the Euler angles φ, θ, and ψ providing a smallest mean squared error with respect to the other vectorcardiogram are established as the rotation of the fetal heart. Preferably a numerical optimization technique is used to reduce the number of tries and/or improve the accuracy.
4. Detection of translational movement of fetus by multilateration. The ECG signal which is produced at a given spot (i.e., the fetal heart) arrives at slightly different times at the different electrode positions on the maternal abdomen. These time differences are calculated, for example by means of cross-correlation. Subsequently these time differences are combined with knowledge of the electrode positions to determine the source of the signals. The multilateration technique is described in relation to GPS systems in "A Synthesizable VHDL Model of the Exact Solution for Three-dimensional Hyperbolic Positioning System", by R. Bucher et al., in: VLSI Design, 2002 Vol. (2), pp. 507-520.

Figure 6:
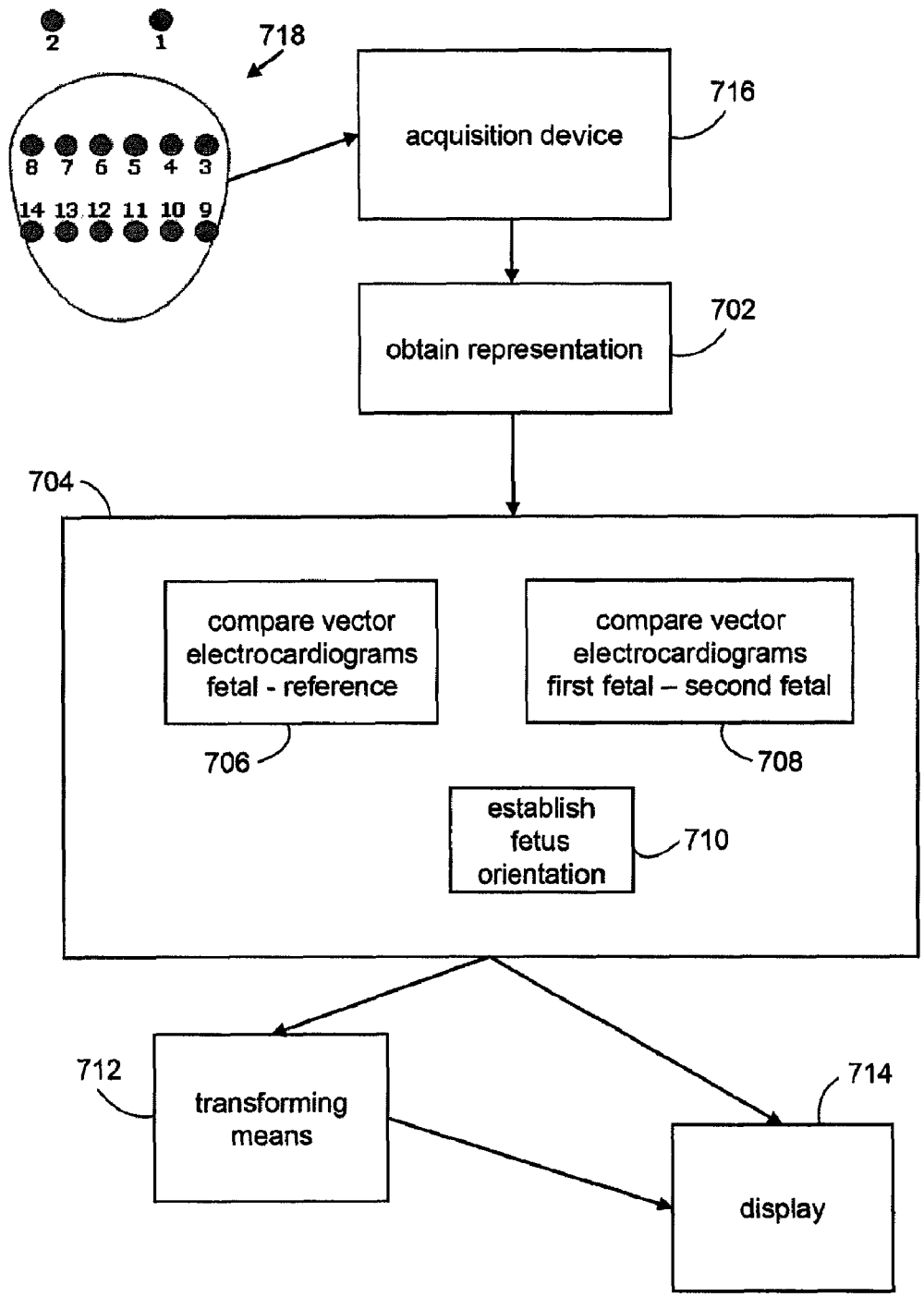
FIG. 6 illustrates an embodiment.

FIG. 6 illustrates a diagram of a system, for example in a cardiac monitoring device, for monitoring a fetus during gestation. The figure schematically shows at 718 a plurality of electrodes 1-14 fixed to a maternal body skin. Electrodes 1 and 2 are for example affixed to the shoulders, whereas electrodes 3-14 are affixed to the abdomen. Other electrode configurations are possible, see for example the configurations 102 and 106 in FIG. 1. However, preferably a plurality of electrodes are attached to the maternal skin close to the fetus. The electrodes are connected to an acquisition device 716 that collects electronic signals measured by the electrodes. Acquisition device 716 may store the signals for further processing and/or forward the signals to a means 702 for obtaining an at least partial representation of a fetal vector electrocardiogram. Preferably, the signals are forwarded to means 702 in real-time. A fetal vector electrocardiogram is indicative of a time path of an electrical field vector generated by the fetal heart. In general such a fetal vector electrocardiogram is three-dimensional in nature, because the direction of the electric field vector generated by the muscle contractions of the heart varies during the cardiac cycle. To obtain the most reliable orientation information, the at least partial representation of the fetal vector electrocardiogram represents this three-dimensional character of the fetal vector electrocardiogram. To reduce computational complexity, the partial representation may, for example, comprise a two-dimensional or a one-dimensional projection of the fetal vector electrocardiogram. The two-dimensional projection is for example a projection on a dorsal plane, because this plane is most easily reconstructed from the electrodes on the abdomen. The at least partial representation of the fetal vector electrocardiogram may be computed as described above, or as described in "Source parameter estimation in inhomogeneous volume conductors of arbitrary shape", by T. Oostendorp, in: Modeling the fetal ECG, Ph.D. thesis, Katholieke Universiteit to Nijmegen, Jan. 19, 1989, pp. 35-54; or as described in "General Theory of Heart-Vector Projection" by E. Frank, in: Circ. Res. 1954; 2; 258-270. The means 702 may comprise a processing unit to perform the signal processing required to obtain the representation. Alternatively, the means 702 may simply comprise an input for receiving the representation.

The electrodes 718 may be any kind of electrodes suitable to measure the electronic signals at the body surface. Standard electrodes are fixed to the body surface. However, other kinds of electrodes such as capacitive electrodes may be employed.

The at least partial representation of the fetal vector electrocardiogram is forwarded to means 704 for establishing orientation information relating to the fetus. This orientation information is extracted from the shape of the fetal vector electrocardiogram. The orientation information may comprise the actual orientation of the fetal heart within the maternal body. The orientation information may also comprise a change of the orientation of the fetal heart within the maternal body. As the orientation of the fetal heart is almost the same in most fetuses, the orientation of the fetal heart is also an indication of the orientation of the fetus. Once the orientation of the heart inside the fetus has been established, for example by combining the fetal vector electrocardiogram with externally acquired ultrasound images, the orientation of the fetal body may be established with higher reliability. Moreover, as the fetal heart is fixed within the fetus, a change of the orientation of the fetal heart corresponds to a change of the orientation of the fetus. Because the electrodes are fixed with respect to the maternal body, the orientation information is in principle relative to the orientation of the maternal body.

In an embodiment, the means 704 for establishing orientation information comprises means 706 for comparing the fetal vector electrocardiogram with a reference vector electrocardiogram. The comparison results in an orientation of the fetal vector electrocardiogram with respect to the reference vector electrocardiogram. For example the at least partial representation of the fetal vector electrocardiogram is matched with a corresponding portion or partial representation or projection of the reference vector electrocardiogram. The reference vector electrocardiogram may be based on an average of vector electrocardiograms of a representative population of fetuses. Preferably the orientation of a fetus is known with respect to the reference vector electrocardiogram. Means 710 then establishes the orientation of the fetus with respect to the predetermined orientation of the reference vector electrocardiogram.

In an embodiment, the orientation information is indicative of a motion of the fetus. For example, a rotational motion is established by a changed orientation of the fetal vector electrocardiogram. A translational motion may be established by finding an origin of the fetal electrocardiograph signals. To this end, the approach of Bucher et al. may be employed. Alternatively, temporal irregularities in the fetal vector electrocardiogram may be analyzed to establish rotational or translational motion and/or muscle contractions.

In an embodiment, the means 704 for establishing orientation information comprises means 708 for comparing first fetal vector electrocardiogram data obtained during a first time interval with second fetal vector electrocardiogram data obtained during a second time interval. This helps to establish the motion of the fetus. For example, by establishing a rotation between the two sets of fetal vector electrocardiogram data, a rotation of the fetus is detected.

The orientation information is output from means 704 to a display 714. The information may also be stored or transferred via a network.

An embodiment comprises means 712 for transforming electrocardiography data into a projected fetal electrocardiogram. This transformation is performed according to a predetermined projection direction that is fixed with respect to the orientation of the fetus. The electrocardiography data comprises the at least partial representation of the fetal vector electrocardiogram. This at least partial representation of the fetal vector electrocardiogram is projected according to a predetermined measurement direction. For example, the projection direction corresponds to a measurement with electrodes attached to a scalp of the fetus, or one of the Van Einthoven leads: Lead I, Lead II, Lead III, or the extremity leads aVR, aVL, or aVF. The projection directions are graphically indicated in FIGS. 2A and 2B. It will be understood that the means 712 takes as its input an at least partial representation of a fetal vectorcardiogram or a two-dimensional projection thereof, or other electrocardiography data, and the orientation of the fetus. Alternatively, the fetal vectorcardiogram is rotated to a fixed orientation before it is provided to the means 712, in which case the orientation of the fetus does not need to be provided as a separate input.

In an alternative embodiment, the means 704 for establishing orientation information is arranged to remove the maternal ECG signal from the measured signals obtained from acquisition device 716, and perform a pattern analysis on the resulting fetal signals. Different presentations and positions of the fetus are associated with different signal patterns. This property may be employed to establish the orientation of the fetus and the fetal heart. See for example WO2005/

039410A1. Moreover, it may be possible to define, for each relevant presentation and/or position and/or orientation of the fetus, a mapping that maps the fetal signals into the fetal ECG corresponding to the predetermined projection direction. Consequently, in an alternative embodiment of means 712 for transforming electrocardiography data into a projected fetal electrocardiogram, the appropriate mapping is applied to the fetal signals in dependence on the established presentation and/or position and/or orientation of the fetus.

In an embodiment, a medical imaging apparatus is made available so a gynecologist or radiologist may establish the orientation of the fetus within the maternal body. Means 706 for determining the orientation of the fetal heart is provided as set forth. Additionally, means are provided for establishing an orientation of the heart of the fetus relative to the body of the fetus. This means uses a difference between the orientation of the body of the fetus established using the medical imaging device and the orientation of the heart of the fetus established using the vector electrocardiogram.

An embodiment comprises a method of monitoring a fetus during gestation, the method comprising obtaining an at least partial representation of a fetal vector electrocardiogram indicative of a time path of an electrical field vector generated by a fetal heart of the fetus; and establishing orientation information relating to the fetus in dependence on a shape of the fetal vector electrocardiogram according to the at least partial representation.

An embodiment comprises a computer program product. It comprises machine executable instructions for causing a processor to perform the steps of:

obtaining an at least partial representation of a fetal vector electrocardiogram indicative of a time path of an electrical field vector generated by a fetal heart of the fetus; and establishing orientation information relating to the fetus in dependence on a shape of the fetal vector electrocardiogram according to the at least partial representation.

In "Monitoring the fetal heart rate and fetal electrocardiogram: abdominal recordings are as good as direct ECG measurements" by R. Vullings et al., Pediatric Research 58(2): 424, August 2005, a project is described with the aim to develop an algorithm to monitor online the fetal heart rate (fHR) and fetal electrocardiogram (fECG) from maternal abdominal recordings. In this project, measurements have been performed using 12 electrodes on the abdomen of the mother. In an initialization phase, the algorithm calculates the fetal signal for each electrode after effectively removing the maternal ECG and suppressing the electromyogram (EMG). Next, the algorithm selects the 4 signals in which the fetal component is most present and uses these signals for further calculations. The reduction of the number of electrodes used in the calculation decreases computation times significantly and enables the algorithm to monitor the fHR online. To increase the signal-to-noise ratio of the calculated fECG-complex, 10 consecutive PQRS-complexes are averaged. By means of cross correlating the PQRS complexes, PQRS-complexes containing artifacts are excluded from the averaging process. The algorithm is validated by comparing the calculated fHR from the abdominal recordings to the fHR determined from direct ECG signals measured with a scalp electrode. The proposed algorithm provides a valuable tool for obtaining noninvasively and online information of the fHR and fECG in stages of pregnancy earlier than labor.

In "The fetal heart rate and sympathetic activity determined non-invasively from the maternal abdomen", by R. Vullings et al., 7th World Congress of Perinatal Medicine, 2005, Zagreb, Croatia, a project is described with the aim to perform spectral analysis on the beat-to-beat fetal heart rate, determined non-invasively from the maternal abdomen, in order to assess information on the activity of the fetal sympathetic and parasympathetic systems. Activity of these systems changes under influence of physiological circumstances and therefore spectral analysis is assumed to supply additional information on the fetal condition. Measurements were performed using 12 electrodes on the abdomen of the mother. A new algorithm was developed to calculate the fetal heart rate on a beat-to-beat basis from these recordings. (This algorithm was validated by comparing the calculated fetal heart rate from the abdominal recordings to the fetal heart rate determined from direct ECG signals measured with a scalp electrode.) Sympathetic activity and parasympathetic activity were determined by calculating the power in the low frequency spectral band (0.04-0.15 Hz) and the high frequency spectral band (0.4-1.5 Hz) using customized spectral bands. The proposed method provides a valuable tool for obtaining non-invasively the fetal heart rate and fetal sympathetic and parasympathetic activity both during labor and in stages of pregnancy earlier than labor.

An alternative embodiment comprises a system for monitoring a fetus during gestation, the system comprising an input for receiving a plurality of electrocardiogram measurements measured at least one position on a surface of a maternal body; and means for processing said plurality of electrocardiogram measurements to obtain a representation of an electric signal produced by the fetus, for example a fetal ECG.

The embodiment may comprise means for establishing a motion of the fetus, for example a movement of one or more limbs of the fetus, in dependence on the representation of the electric signal produced by the fetus.

The embodiment may comprise means for establishing a muscle contraction by the fetus in dependence on the representation of the electric signal produced by the fetus.

Variations in heart rate and irregularities in the shape of the fetal ECG signal are correlated to motion of the fetus and muscle contraction. By monitoring these variations and irregularities, the frequency, duration and/or intensity of the movements and/or muscle contractions may be established and monitored. This is a particularly efficient way of monitoring muscle contractions and limb movements, because it can be automated and does not depend on an observing physician, e.g. gynecologist or radiologist and/or subjective assessment by the mother.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines.

Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for monitoring a fetus during gestation, the system comprising
   an input for receiving a plurality of electric signals measured on a surface of a maternal body; and
   means for providing an at least partial representation of a fetal vector electrocardiogram in dependence on the plurality of electric signals and indicative of a time path of an electrical field vector generated by a fetal heart of the fetus,
   means for establishing orientation information relating to the fetus in dependence on a shape of the fetal vector electrocardiogram according to the at least partial representation, and
   means for providing a fetal electrocardiogram based on the received electric signals and based on an orientation of the fetus, wherein the fetal electrocardiogram represents a projection of a fetal cardiac potential vector according to a predetermined projection direction that is fixed with respect to the fetus, and wherein the means for providing a fetal electrocardiogram is arranged for projecting the fetal vector electrocardiogram according to the projection direction.

2. The system according to claim 1, wherein the means for proving a fetal electrocardiogram is arranged to provide signals corresponding to standard leads which may be connected to an input of existing medical equipment.

3. The system according to claim 1, wherein the projection direction corresponds to a measurement made with electrodes, when the electrodes are attached to a scalp of the fetus.

4. The system according to claim 1, wherein the projection direction corresponds to at least one direction associated with the Van Einthoven triangle: Lead I, Lead II, Lead III, aVR, aVL, or aVF.

5. The system according to claim 1, further comprising a display for displaying the orientation information and/or the fetal electrocardiogram.

6. The system according to claim 5, wherein the orientation information is indicative of an orientation of the fetus.

7. The system according to claim 5, wherein the means for establishing orientation information comprises means for comparing the fetal vector electrocardiogram with a reference vector electrocardiogram to establish an orientation of the fetal vector electrocardiogram with respect to the reference vector electrocardiogram.

8. The system according to claim 7, wherein the reference vector electrocardiogram is associated with a predetermined orientation, and wherein the means for establishing orientation information comprises means for establishing an orientation of the fetus with respect to the predetermined orientation.

9. The system according to claim 5, wherein the orientation information is indicative of a motion of the fetus.

10. The system according to claim 9, wherein the means for establishing orientation information comprises means for comparing first fetal vector electrocardiogram data obtained during a first time interval with second fetal vector electrocardiogram data obtained during a second time interval to establish the motion of the fetus.

11. The system according to claim 5, wherein the orientation information is indicative of an orientation of the fetal heart.

12. The system according to claim 5, wherein at least part of the orientation information is relative to an orientation of a maternal body bearing the fetus.

13. The system according to claim 1, wherein the means for obtaining the fetal vector electrocardiogram comprises a plurality of electrodes arranged for being positioned close to a surface of a maternal body bearing the fetus.

14. The system according to claim 13, wherein at least one of the electrodes comprises a capacitive electrode.

15. The system according to claim 1, wherein the means for obtaining the fetal vector electrocardiogram comprises signal processing means for transforming signals from a plurality of electrodes that are arranged for being positioned close to a surface of a maternal body bearing the fetus into the fetal vector electrocardiogram.

16. The system according to claim 15, wherein the signal processing means comprises a means for removing a maternal electrocardiography signal from at least one of the signals obtained from the plurality of electrocardiography electrodes.

17. The system according to claim 1, wherein the orientation information is indicative of an orientation of a heart of the fetus, and further comprising
   a medical imaging apparatus for establishing an orientation of a body of the fetus; and means for establishing an orientation of the heart of the fetus relative to the body of the fetus using a difference between the orientation of the body of the fetus established using the medical imaging device and the orientation of the heart of the fetus established using the vector electrocardiogram.

18. The system according to claim 1, wherein the system further comprises at least one of:
a display for showing the established information;
a recorder for storing the established information; or
an output for transmitting the established information to another device.

19. A method of monitoring a fetus during gestation, the method comprising:
receiving at an input a plurality of electric signals measured on a surface of a maternal body;
using a processor to:
provide an at least partial representation of a fetal vector electrocardiogram in dependence on the plurality of electric signals and indicative of a time path of an electrical field vector generated by a fetal heart of the fetus,
establish orientation information relating to the fetus in dependence on a shape of the fetal vector electrocardiogram according to the at least partial representation,
provide a fetal electrocardiogram based on the received electrical signals and based on an orientation of the fetus, wherein the fetal electrocardiogram represents a projection of a fetal cardiac potential vector according to a predetermined projection direction that is fixed with respect to the fetus, and
project the fetal vector electrocardiogram according to the projection direction.

20. A non-transitory computer program product comprising machine executable instructions for causing a processor to perform the method according to claim 19.

* * * * *